United States Patent
Cross, Jr.

(10) Patent No.: US 7,184,838 B2
(45) Date of Patent: Feb. 27, 2007

(54) IMPLANTABLE MEDICAL LEAD AND METHOD OF MANUFACTURE

(75) Inventor: Thomas E. Cross, Jr., St. Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 330 days.

(21) Appl. No.: 10/957,456

(22) Filed: Oct. 1, 2004

(65) Prior Publication Data

US 2005/0113899 A1    May 26, 2005

Related U.S. Application Data

(60) Provisional application No. 60/508,018, filed on Oct. 2, 2003.

(51) Int. Cl.
*A61N 1/00* (2006.01)
(52) U.S. Cl. ...................... 607/116; 607/115
(58) Field of Classification Search ............. 607/115, 607/116, 119; 174/73.1, 86–87; 439/449
See application file for complete search history.

(56) References Cited

U.S. PATENT DOCUMENTS

| | | | |
|---|---|---|---|
| 4,484,586 A | 11/1984 | McMickle et al. | |
| 4,782,834 A | 11/1988 | Maguire et al. | |
| 4,840,186 A | 6/1989 | Lekholm et al. | |
| 4,945,342 A | 7/1990 | Steinemann | |
| 5,016,646 A | 5/1991 | Gotthardt et al. | |
| 5,324,327 A | 6/1994 | Cohen | |
| 5,330,521 A | 7/1994 | Cohen | |
| 5,354,327 A | 10/1994 | Smits | |
| 5,411,527 A | 5/1995 | Alt | |
| 5,433,730 A | 7/1995 | Alt | |
| 5,483,022 A | 1/1996 | Mar | |
| 5,571,157 A | 11/1996 | McConnell | |
| 5,591,142 A | 1/1997 | Van Erp | |
| 5,796,044 A | 8/1998 | Cobian et al. | |
| 5,797,905 A | 8/1998 | Fleischman et al. | |
| 5,800,496 A | 9/1998 | Swoyer et al. | |
| 5,810,802 A | 9/1998 | Panescu et al. | |
| 5,810,867 A | 9/1998 | Zarbatany et al. | |
| 5,827,296 A | 10/1998 | Morris et al. | |
| 5,843,148 A | 12/1998 | Gijsbers et al. | |
| 5,843,149 A | 12/1998 | Ebert et al. | |
| 5,853,652 A | 12/1998 | Schildgen et al. | |
| 5,865,843 A | 2/1999 | Baudino | |
| 5,871,530 A | 2/1999 | Williams et al. | |

(Continued)

FOREIGN PATENT DOCUMENTS

EP    0769308    4/1997

(Continued)

*Primary Examiner*—Robert E. Pezzuto
*Assistant Examiner*—Brian T. Gedeon
(74) *Attorney, Agent, or Firm*—Stephen W. Bauer (57) ABSTRACT

An implantable electrical lead having coiled conductors and a method of manufacturing the lead. The method generally comprises: (a) assembling, along an outer surface of inner elongate structure defining an longitudinal axis, at least one elongate conductor and at least one twist ring holding a first portion of the elongate conductor; (b) fixing a second portion of the elongate conductor to the outer surface of the inner elongate structure, the second portion of the elongate conductor being spaced along the length of the elongate conductor; and (c) rotating the twist ring relative to the longitudinal axis of the inner elongate structure to coil the at least one elongate conductor.

44 Claims, 6 Drawing Sheets

U.S. PATENT DOCUMENTS

| | | |
|---|---|---|
| 5,876,430 A | 3/1999 | Shoberg et al. |
| 5,891,114 A | 4/1999 | Chien et al. |
| 5,897,584 A | 4/1999 | Herman |
| 5,919,222 A | 7/1999 | Hjelle et al. |
| 5,948,539 A | 9/1999 | Paulsen et al. |
| 5,952,403 A | 9/1999 | Paulsen et al. |
| 5,954,759 A | 9/1999 | Swoyer et al. |
| 5,957,970 A | 9/1999 | Shoberg et al. |
| 5,964,795 A | 10/1999 | McVenes et al. |
| 5,967,977 A | 10/1999 | Mullis et al. |
| 5,968,086 A | 10/1999 | Bonner et al. |
| 5,968,087 A | 10/1999 | Hess et al. |
| 5,987,746 A | 11/1999 | Williams |
| 5,991,650 A | 11/1999 | Swanson et al. |
| 5,999,858 A | 12/1999 | Sommer et al. |
| 6,016,436 A | 1/2000 | Bischoff et al. |
| 6,018,683 A | 1/2000 | Verness et al. |
| 6,026,567 A | 2/2000 | Swoyer et al. |
| 6,030,382 A | 2/2000 | Fleischman et al. |
| 6,038,463 A | 3/2000 | Laske et al. |
| 6,040,369 A | 3/2000 | Paulsen et al. |
| 6,049,736 A | 4/2000 | Stewart et al. |
| 6,052,625 A | 4/2000 | Marshall |
| 6,061,598 A | 5/2000 | Verness et al. |
| 6,076,019 A | 6/2000 | Rutten |
| 6,106,522 A | 8/2000 | Fleischman et al. |
| 6,119,042 A | 9/2000 | Verness et al. |
| 6,129,724 A | 10/2000 | Fleischman et al. |
| 6,144,882 A | 11/2000 | Sommer et al. |
| 6,165,163 A | 12/2000 | Chien et al. |
| 6,178,355 B1 | 1/2001 | Williams et al. |
| 6,197,021 B1 | 3/2001 | Panescu et al. |
| 6,245,068 B1 | 6/2001 | Olson et al. |
| 6,256,542 B1 | 7/2001 | Marshall et al. |
| 6,263,249 B1 | 7/2001 | Stewart et al. |
| 6,278,897 B1 | 8/2001 | Rutten et al. |
| 6,280,433 B1 | 8/2001 | McIvor et al. |
| 6,285,910 B1 | 9/2001 | Verness et al. |
| 6,295,476 B1 | 9/2001 | Schaenzer |
| 6,357,447 B1 | 3/2002 | Swanson et al. |
| 6,379,346 B1 | 4/2002 | McIvor et al. |
| 6,397,108 B1 | 5/2002 | Camps et al. |
| 6,434,431 B1 | 8/2002 | Camps et al. |
| 6,471,699 B1 | 10/2002 | Fleischman et al. |
| 6,477,427 B1 | 11/2002 | Stolz et al. |
| 6,489,562 B1 | 12/2002 | Hess et al. |
| 6,500,172 B1 | 12/2002 | Panescu et al. |
| 6,501,991 B1 | 12/2002 | Honeck et al. |
| 6,501,992 B1 | 12/2002 | Belden et al. |
| 6,516,230 B2 | 2/2003 | Williams et al. |
| 6,549,812 B1 | 4/2003 | Smits |
| 6,556,873 B1 | 4/2003 | Smits |
| 6,562,021 B1 | 5/2003 | Derbin et al. |
| 6,567,704 B2 | 5/2003 | Sundquist et al. |
| 6,615,695 B1 | 9/2003 | Hjelle et al. |
| 2001/0014770 A1 | 8/2001 | Olson et al. |
| 2001/0029395 A1 | 10/2001 | Stewart et al. |
| 2001/0044646 A1 | 11/2001 | Marshall et al. |
| 2002/0049485 A1 | 4/2002 | Smits |
| 2002/0065544 A1 | 5/2002 | Smits |
| 2002/0068965 A1 | 6/2002 | Sass |
| 2002/0099430 A1 | 7/2002 | Verness |
| 2002/0115343 A1 | 8/2002 | Sommer et al. |
| 2002/0177888 A1 | 11/2002 | Williams et al. |
| 2002/0193790 A1 | 12/2002 | Fleischman et al. |
| 2003/0045786 A1 | 3/2003 | Zhao et al. |
| 2003/0045920 A1 | 3/2003 | Belden et al. |
| 2003/0050680 A1 | 3/2003 | Gibson et al. |
| 2003/0065322 A1 | 4/2003 | Panescu et al. |
| 2003/0073348 A1 | 4/2003 | Ries et al. |
| 2003/0077935 A1 | 4/2003 | Stein et al. |
| 2003/0105505 A1 | 6/2003 | Pianca |
| 2003/0143895 A1 | 7/2003 | Sommer et al. |
| 2004/0162601 A1 | 8/2004 | Smits |

FOREIGN PATENT DOCUMENTS

| | | |
|---|---|---|
| EP | 0620022 | 2/1999 |
| EP | 0955917 | 11/1999 |
| EP | 1174886 | 1/2002 |
| WO | WO 92/13483 | 8/1992 |
| WO | WO 94/07549 | 4/1994 |
| WO | WO 95/08366 | 3/1995 |
| WO | WO 95010318 | 4/1995 |
| WO | WO 0102047 | 1/2001 |
| WO | WO 01/74443 | 10/2001 |
| WO | WO 01097903 | 12/2001 |
| WO | WO 2003/022352 | 3/2003 |

IMPLANTABLE MEDICAL LEAD AND METHOD OF MANUFACTURE

RELATED APPLICATIONS

This application claims priority to U.S. Provisional Application No. 60/508,018, filed Oct. 2, 2003, which is hereby incorporated herein by reference in its entirety.

FIELD

This invention relates to a medical device and more particularly to implantable neurological electrical stimulators and implantable electrical stimulation leads.

BACKGROUND

The medical device industry produces a wide variety of electronic and mechanical devices for treating patient medical conditions such as pacemakers, defibrillators, neurostimulators and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition and a fuller life. One type of medical device is an implantable neurological stimulation system that can be used to treat conditions such as pain, movement disorders, pelvic floor disorders, gastroparesis, and a wide variety of other medical conditions. The neurostimulation system typically includes a neurostimulator, a stimulation lead, and an extension such as shown in Medtronic, Inc. brochure "Implantable Neurostimulation System" (1998). More specifically, the neurostimulator system can be an Itrel II™ Model 7424 or an Itrel 3™ Model 7425 available from Medtronic, Inc. in Minneapolis, Minn. that can be used to treat conditions such as pain, movement disorders and pelvic floor disorders. The neurostimulator is typically connected to a stimulation lead that has one or more electrodes to deliver electrical stimulation to a specific location in the patient's body.

Current leads that incorporate straight, silver cored, bundled-stranded-wire ("bsw") wire have the weakness that all axial loading is transmitted, through the wires, to the electrical connections at either end of the device. Historically, coiled conductor designs absorbed much of the loading in the stretching of the coil. Additionally, existing lead body configurations are of a constant stiffness, distal to proximal ends. This brings about the compromise to find a stiffness that is suitable for the most rigorous requirement for the application. An example of this is the desire to stiffen the proximal end of the lead body to allow insertion through seal rings and ball seal connectors, while at the same time providing a lead body stiffness consistent with currently established neurological lead standards. For the most part, these are different requirements. A variable stiffness is desirable.

SUMMARY

Among other things, an exemplary embodiment of a lead body is provided that has variable stiffness and provides both the flex life of the current, low impedance, BSW family of leads as well as a coiled conductor configuration that minimizes the loading of the electrical connections at either end of that configuration.

A first exemplary embodiment of the invention is a method of manufacturing an implantable electrical lead body. The method generally comprises: (a) assembling, along an outer surface of inner elongate structure defining an longitudinal axis, at least one elongate conductor and at least one twist ring holding a first portion of the elongate conductor; (b) fixing a second portion of the elongate conductor to the outer surface of the inner elongate structure, the second portion of the elongate conductor being spaced along the length of the elongate conductor; and (c) rotating the twist ring relative to the longitudinal axis of the inner elongate structure to coil the at least one elongate conductor.

The step of assembling, along an outer surface of inner elongate structure defining an longitudinal axis, at least one elongate conductor and at least one twist ring holding a first portion of the elongate conductor may be performed before, during or after the step of fixing a second portion of the elongate conductor to the outer surface of the inner elongate structure, the second portion of the elongate conductor being spaced along the length of the elongate conductor.

In a second embodiment of the method, the method generally comprises: (a) providing an elongate strut, first and second twist rings, and at least one conductor, the first and second twist rings having at least one opening or groove for receiving and holding at least one conductor; (b) fixing the first twist ring to the strut; (c) threading the at least one conductor wire through the opening or groove in the first twist ring; (d) placing a second twist ring on the strut wherein upon conclusion of steps (b) and (d) the first and second twist rings are spaced apart along the strut; (e) threading the at least one conductor through the opening or groove in the second twist ring, wherein steps (b) through (e) may be performed in any order and upon conclusion of steps (b) through (e) a segment of the at least one conductor is defined between the first and second twist rings; (f) rotating the second twist ring relative to the longitudinal axis of the strut to coil the segment of at least one elongate conductor between the first and second twist rings; and (g) fixing the second twist ring to the strut.

In a preferred exemplary embodiment of the second exemplary method, an outer jacket is placed over the strut before only one of steps (b) of fixing the first twist ring to the strut, and (d) of placing the second twist ring to the strut. For example, the outer jacket may be placed over the strut is performed after step (b) of fixing the first twist ring to the strut and before step (d) of placing the second twist ring to the strut.

In two alternative preferred versions of the second exemplary method, the outer jacket may be placed over the strut before or after step (c) of threading the at least one conductor wire through the opening or groove in the first twist ring. The first and second twist rings may be fixed to the strut by bonding, adhesive, mechanical fixation or otherwise.

In a preferred exemplary embodiment, the second exemplary method further includes: (h) placing a third twist ring on the strut wherein upon conclusion of steps (b), (c) and (h) the first, second and third twist rings are spaced apart along the strut, the third twist ring having an opening or groove; (i) threading the at least one conductor through the opening or groove in the third twist ring, wherein steps (b) through (e) and (h) through (i) may be performed in any order and upon conclusion thereof a second segment of the at least one conductor is defined between the third twist ring and one of the first and second twist rings; (j) rotating the third twist ring relative to the longitudinal axis of the strut to coil the second segment of the at least one elongate conductor at a second pitch or second direction of wind different than the first pitch or first direction of wind; and (g) fixing the third twist ring to the strut. This preferred exemplary embodiment may also optionally include: (k) before only one of steps (b) of fixing the first twist ring to the strut, and (d) of placing the second twist ring to the strut, placing a first outer jacket portion over the strut such that upon conclusion of steps (b) and (d) the first outer jacket portion is arranged between the first and second twist rings; and (l) before the step (h) of placing the third twist ring, placing a second outer jacket portion over the strut such that upon conclusion of steps (b), (d) and (h) the second outer jacket portion is arranged between the third twist ring and one of the first and second twist rings.

A second exemplary embodiment of the invention is an implantable electrical lead. The implantable electrical lead generally comprises proximal and distal end portions, and a lead body extending between the proximal and distal end portions. At least one electrical contact in the proximal end portion is adapted to make electrical contact with a connector of a lead extension or pulse generator. At least one electrode in the distal end portion is adapted to interact with tissue. At least one elongate conductor extends through the lead body between the proximal and distal portions in electrical communication with the contact and electrode. The conductor includes along its length at least a first portion, a second portion spaced along the length of conductor from the first portion, and a first segment defined between the first and second portion. The lead body includes an inner elongate structure defining an longitudinal axis, and first and second twist rings mounted on the inner elongate structure. The first and second twist rings hold the first and second portions, respectively, of the elongate conductor. During manufacture of the lead, one of the first and second twist rings has been rotated about the inner elongate structure relative to the other of the first and second twist rings to coil the first segment of the elongate-conductor, and both twist rings have been bonded to the inner elongate structure. An outer jacket covers the inner elongate structure and first segment of the elongate conductor between the first and second twist rings.

DETAILED DESCRIPTION OF EXEMPLARY EMBODIMENTS

Figure 1:
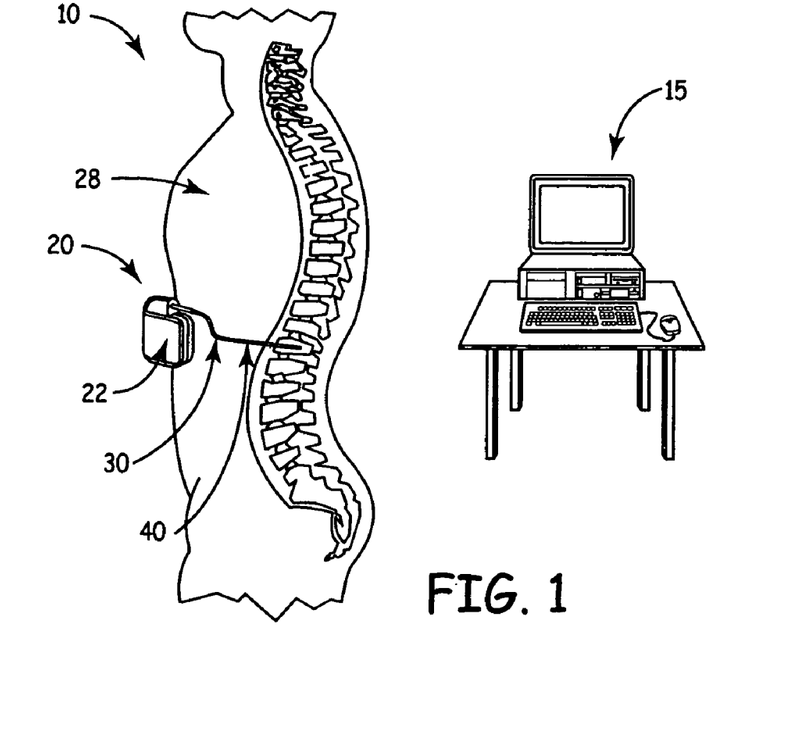
FIG. 1 shows a general environmental view for a neurostimulation system embodiment.

FIG. 1 shows a general environmental view 10 for an implantable neurostimulation system embodiment. Neurostimulation systems are used to treat conditions such as pain, movement disorders, pelvic floor disorders, gastroparesis, and a wide variety of other medical conditions. The neurostimulation system 20 includes a neurostimulator 22 such as an Itrel II® Model 7424 or an Itrel 3® Model 7425 available from Medtronic, Inc. in Minneapolis, Minn., a stimulation lead extension 30, and a stimulation lead 40. The neurostimulator 22 is typically implanted subcutaneously in the patient's body 28 at a location selected by the clinician. The stimulation lead 40 is typically fixed in place near the location selected by the clinician using a device such as the adjustable anchor.

Figure 2:
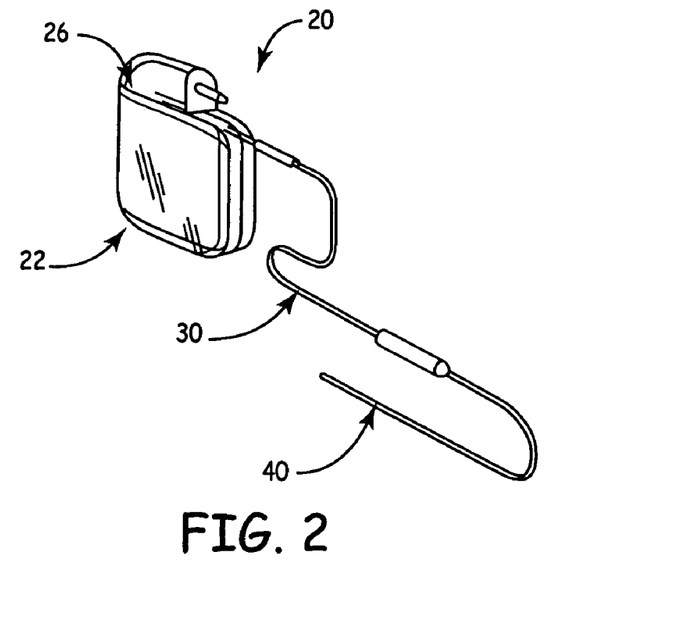
FIG. 2 shows a neurostimulation system embodiment.

FIG. 2 shows an implantable neurostimulation system 20 comprising an implantable neurostimulator 22, as stimulation lead 40, and a lead extension 30. The implantable neurostimulator 22 has a housing, a power supply carried in the housing 24, and stimulation electronics coupled to the battery and coupled to a connector block 26, which is also known as a terminal block. The stimulation lead 40 has a lead proximal end 45, a lead distal end 41 and a lead body 43. The lead proximal end 45 has at least one electrical connector 46 (also known as electrical terminals) and the lead distal end 41 has at least one stimulation electrode 42. There is at least one lead conductor 50 contained in the lead body 43 that is electrically connecting the electrical connector 46 to the stimulation electrode 42.

An implantable neurological stimulation or monitoring system comprises an implantable neurological stimulator 22 or neurological monitor, an implantable neurological lead 40, and at least one electrode 42. The implantable neurological stimulator 22 can be a Medtronic Itrel II® Model 7424 or an Itrel 3® Model 7425 or the like, both of which are commercially available. The neurological monitor 15 can be a Medtronic Neurodiagnostics Keypoint monitoring system.

The implantable neurological lead 40 comprises a lead proximal end 45, a lead distal end 41, at least one conductor 50, at least one electrode 42, and at least one electrical connector 46. The lead proximal end 45 contains at least one electrical connector or contact 46 (e.g., a plurality of such contacts, such as 4, 8, 16 or more) that couples to the implantable neurological stimulator 22 or neurological monitor. The lead distal end 41 contains at least one electrode 42 but preferably a plurality of such electrodes (e.g., 4, 8, 16, etc.).

The conductor 50 is contained in the lead 40 and extends from the lead proximal end 45 to the lead distal end 41. The conductor 50 may, for example, be stranded (made up of many small wires), braided-stranded or "BSW" (braided of many small wires), or solid (made up of one piece).

The conductor 50 being electrically insulated by a polymer. The polymer could be, but is not limited to, ethylene tetrafluoroethylene (ETFE), polytetrafluoroethylene (PTFE), silicone rubber or polyurethane. Other materials that act as electrical insulators can be used. The electrical connector 46 is carried on the lead proximal end 45 and electrically connected to the conductor 50. The neurological lead 40 can be configured as a neurological stimulation lead, a neurological sensing lead, and a combination of both as a neurological stimulation and sensing lead.

Figure 3:
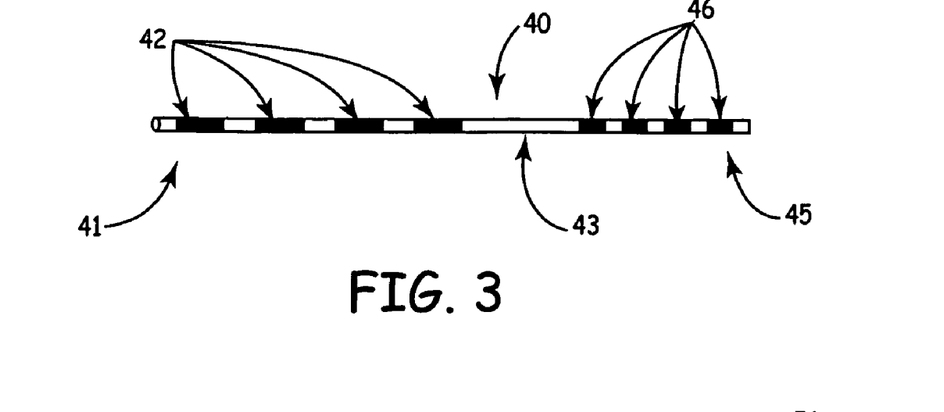
FIG. 3 shows a neurostimulation lead embodiment.

FIG. 3 shows an implantable neurostimulation lead 40 embodiments that have a lead proximal end 45, a lead distal end 41 and a lead body 43. The lead proximal end 45 has at least one electrical contact 46 for connecting to a lead extension 30 or neurostimulator connector block 26. The lead distal end 41 has at least one stimulation electrode 42. The lead body 43 carries at least one conductor 50 electrically connecting the lead proximal electrical contact 46 with the lead distal end 41 stimulation electrode 42.

The lead body 43 can be composed of a wide variety of materials and configurations. Materials may include, but not be limited to silicone rubber, polyurethane, fluoropolymers and the like. Configurations could include monolumen and multilumen tubings. The conductor 50 that electrical connects the lead proximal end 45 electrical contact 46 with the lead distal end 41 stimulation electrode 42 can be composed of a wide variety of material and configurations. Materials may include, but not be limited to MP35N, silver drawn filled tubing (Ag-DFT), Platinum iridium alloys, platinum and the like. Configurations could include stranded, braided or solid wire configured in linear or helical coil arrangements.

The adjective "coiled" defines a structure spirally wound in a continuous series of loops. The noun "coil" refers to that segment of a coiled structure that encompasses 360 degrees of rotation about the axis of the coiled structure. The verb "coil" refers to the act of creating a coiled structure.

The "pitch" is defined as the interval (distance) distance from center to center of the wire in adjacent coils. The pitch may be measured as an average pitch over a plurality (e.g., ten) coils, which may be a particularly convenient way to measure pitch for small pitches.

The "direction of wind" refers to the fact that coils can be wound in either the left-hand (CW) or right-hand (CCW) direction.

A "filar" is one wire. A "unifilar" coil is wound with a single continuous wire. A "mulifiler" coil is wound with more than one filar.

Figure 5:
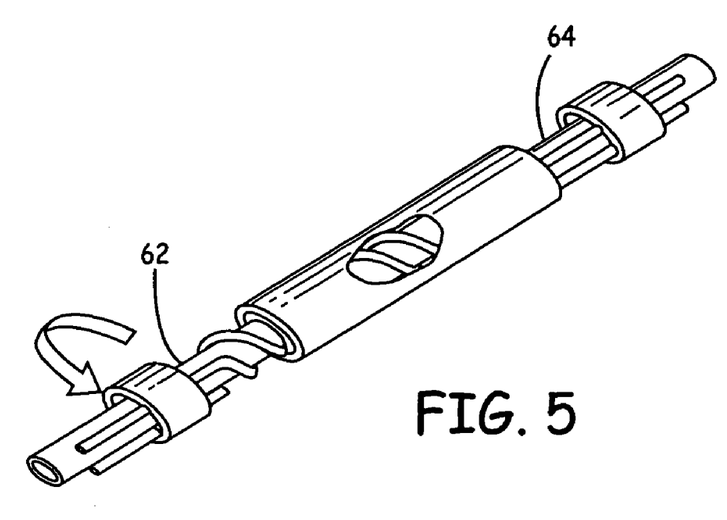

In an exemplary embodiment the conductors 50 includes at least one segment that is coiled at a first pitch (as illustrated in FIG. 5), although various exemplary embodiments involve multiple segments in which the conductor is coiled at different pitches, or in different directions (i.e. a left handed coiled structure versus right handed coiled structure).

Exemplary embodiments allow a conversion from straight, miniature cables to a coiled configuration as part of the manufacturing process. This may be accomplished through the use a pair of extruded twist rings that allow the straight conductor to be twisted to a helical configuration after the outer jacket has been installed as illustrated in FIG. 3.

One of the twist rings 52 may be attached (bonded) to the center strut 56 of the lead body 43 and the conductors 50 are fed through its openings or grooves 58. The lead body outer jacket 60 and the second twist ring 54 are placed on the strut 56 after the conductors 50 are fed through the holes or grooves 58 in the twist ring 52 or 54. By holding the strut 56 stationary (the twist ring 52 is also stationary since it is bonded to the strut 56) and rotating the second twist ring 54, twist in the conductor 50 may be generated to any level desired (e.g., pitch or direction of wind). The second twist ring 54 is in then bonded to the strut 56. See FIG. 5.

Figure 8:
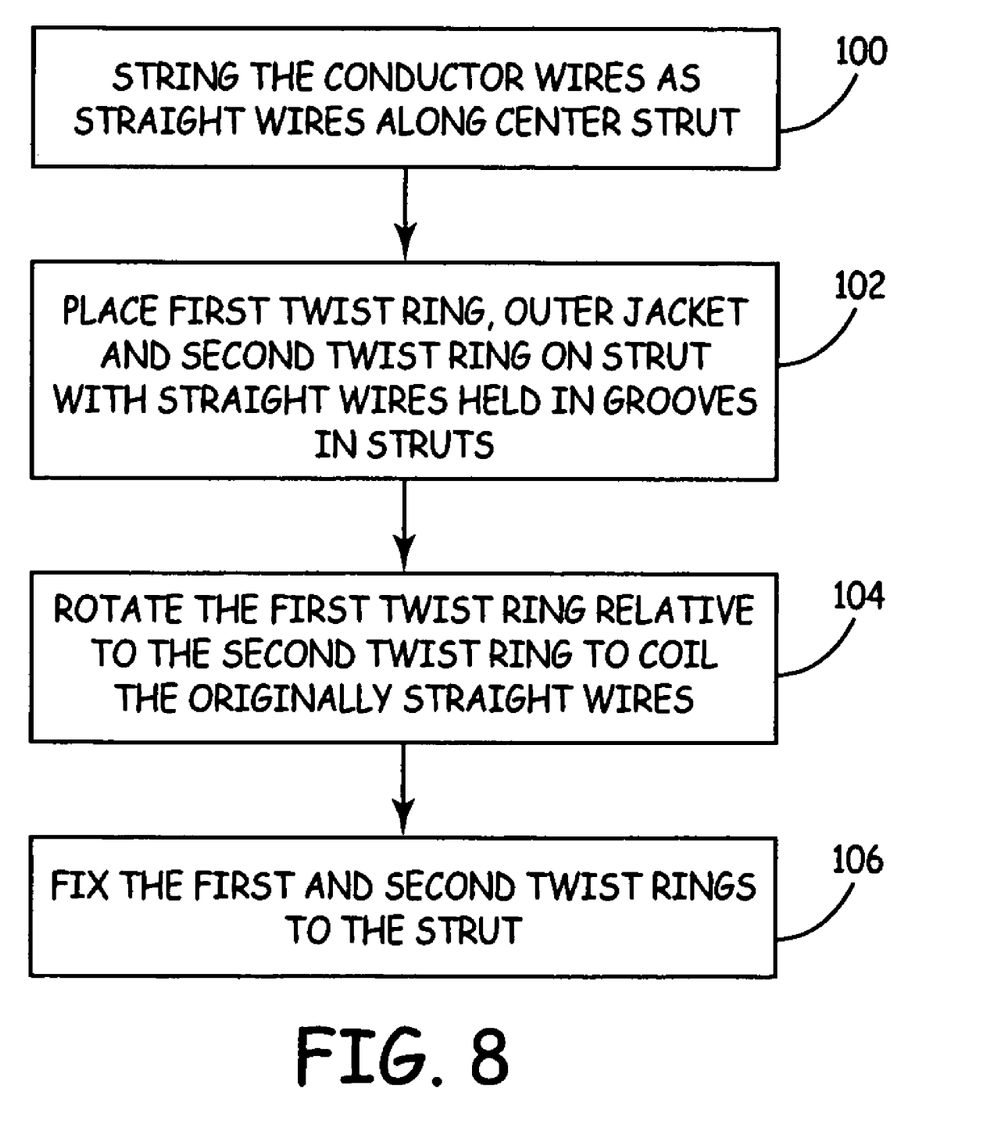
FIGS. 8–10 illustrate exemplary preferred embodiments of the method of the invention, and although provide in flow chart format are not intended to limit the method to any particular order of the illustrated steps.

A preferred exemplary method for manufacturing the lead body is illustrated in FIG. 8. This exemplary method involves (a) stringing the conductor wires 50 as straight wires along center strut 56 in step 100; (b) placing the first twist ring 52, outer jacket 60 and second twist ring 54 on the strut 56 with the straight wires 50 held in grooves 58 in struts in step 102; (c) rotating the first twist ring 52 relative to the second twist ring 54 to coil the originally straight wires in step 104; and (d) fixing the first and second twist rings 52 and 54 to the strut 56 in step 106. Of course, the order of these steps may be changed or overlap.

Figure 10:
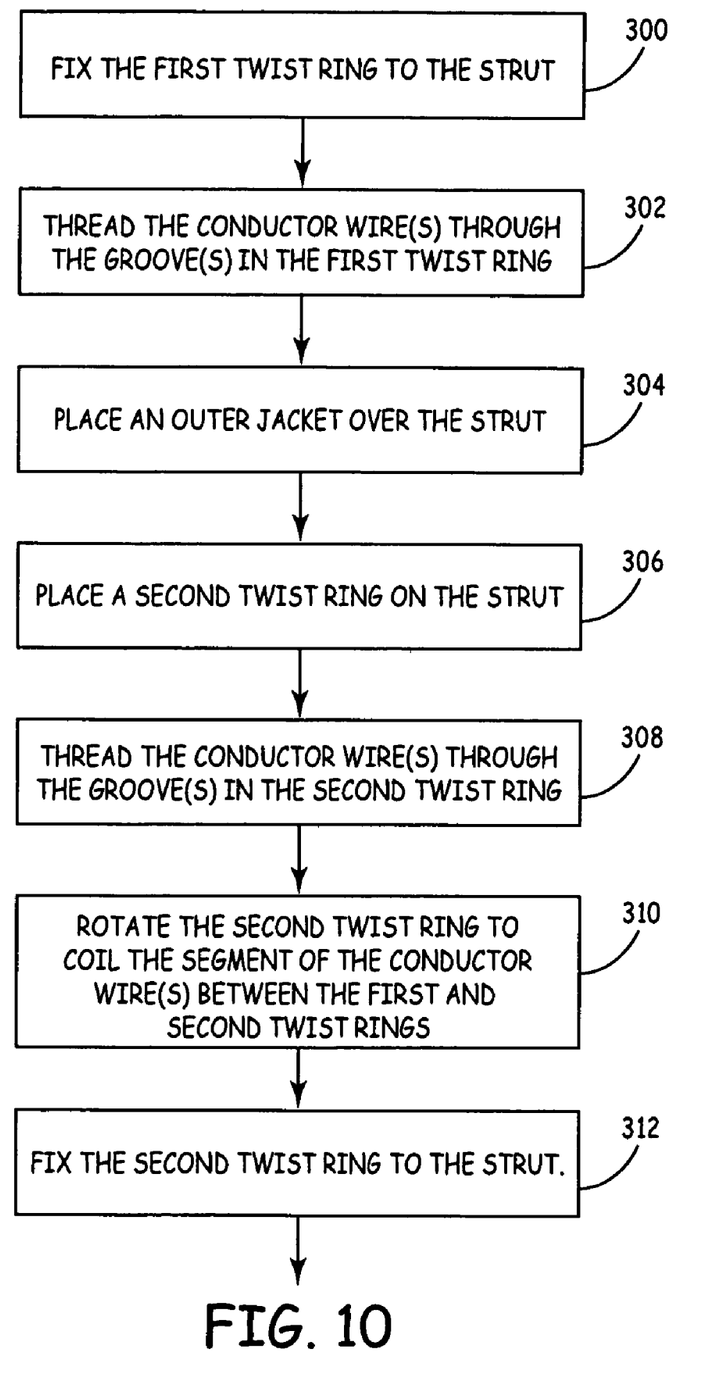

A second preferred exemplary illustration of the method is illustrated in FIG. 10. This exemplary method involves (a) fixing the first twist ring 52 to the strut 56 in step 300; (b) threading the conductor wire(s) 50 through the groove(s) 58 in the first twist ring 52 in step 302; (c) placing an outer jacket 60 over the strut 56 in step 304; (d) placing a second twist ring on the strut in step 306; (e) threading the conductor wire(s) through the groove(s) in the second twist ring in step 308; (f) rotating the second twist ring to coil the segment of the conductor wire(s) between the first and second twist rings in step 310; and (g) fixing the second twist ring to the strut in step 312. Of course, the order of these steps may be changed or overlap. For example, the order to steps 300–308 may readily be varied among themselves so long as steps 310 and 312 are after steps 300, 302, 306 and 308.

Figure 4:
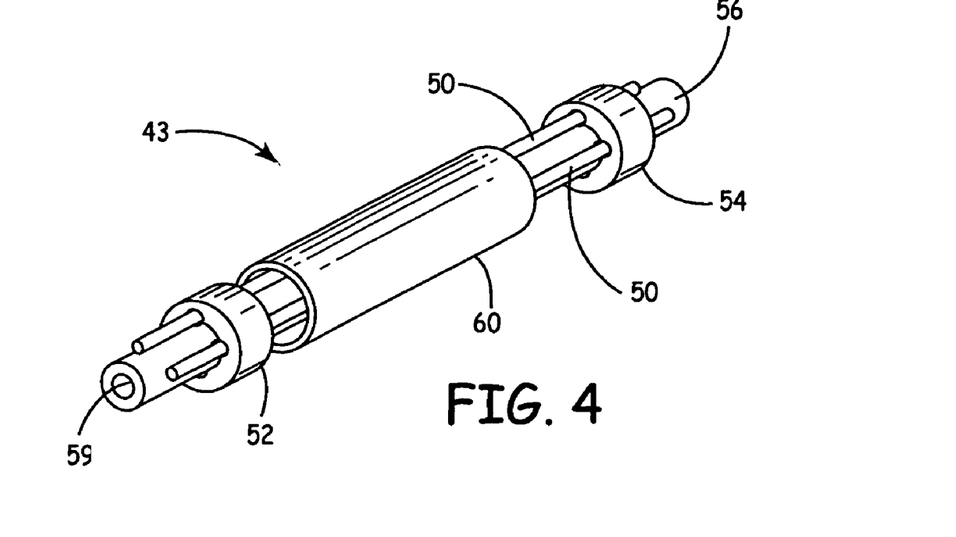
FIGS. 4 and 5 illustrate a preferred embodiment of the method, in which the originally straight conductors are coiled (note that FIG. 5 also illustrates use of strut sections having different stiffnesses).

FIGS. 4 and 5 show two conductors 50 and four wire-holding grooves or openings 58, although it will be understood that the number of conductors 50 and wire-holding grooves or openings 58 may be more or less. Without limiting the possible number variations, certain exemplary embodiments may be suitable for four, eight or sixteen conductors.

To create a lead body 43 of variable stiffness, strut sections 62 and 64 (FIG. 5) of differing stiffness or durometers may be butt glued or bonded together to produce a final device with the desired stiffness at each location. For example, a 75D, proximal end section (Strut 1, FIG. 5) may be bonded to a 55D or 80A section (Strut 2, FIG. 5) to produce the center section of the lead body and a 65D section may then be attached for an application where a slightly stiffer distal end is required. As used herein, "butt glued," "butt bonded" or "butt joint" merely refer to an end-to-end bond or joint between two elongate structures, and is not limited to square-cut joints or such bonds or joints in which the plane of the joint is at a right angle to the longitudinal axis of the elongate structures.

Preferred embodiments allow traditional lead body anchors to be used.

As illustrated in FIG. 8, in an exemplary embodiment of the method, at least one elongate conductor 50 and at least one (first) twist ring 52 holding a first portion of the elongate conductor 50 are assembled along an outer surface of inner elongate structure 56, such as a central strut. A second portion of the elongate conductor 50 is fixed to the outer surface of the inner elongate structure 50, with the second portion of the elongate conductor being spaced along the length of the elongate conductor from the first twist ring 52. The twist ring 52 is rotated relative to the longitudinal axis of the inner elongate structure 56 to coil the at least one elongate conductor 50.

The order of assembling the first twist ring 52, conductor(s) 50 and strut 56 together, fixing the second portion of the conductor 50 to the strut, may be varied based on various processing objectives. For example, the elongate conductor and at least one twist ring may be assembled along an outer surface of inner elongate structure before, during or after the step of fixing a second portion of the elongate conductor to the inner elongate structure.

Preferably, the second portion of the elongate conductor is fixed to the inner elongate structure 56 by a second twist ring 54, which may be bonded or otherwise fixed to the inner elongate structure 56.

Figure 6:
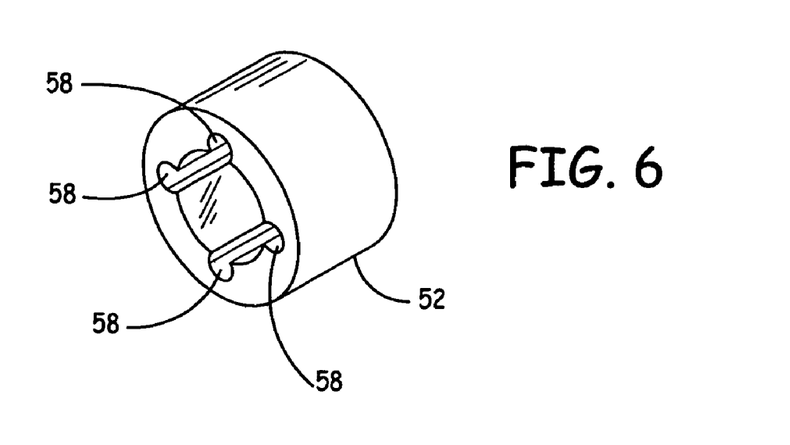
FIG. 6 illustrates an exemplary embodiment of a twist ring having wire grooves.
Figure 7:
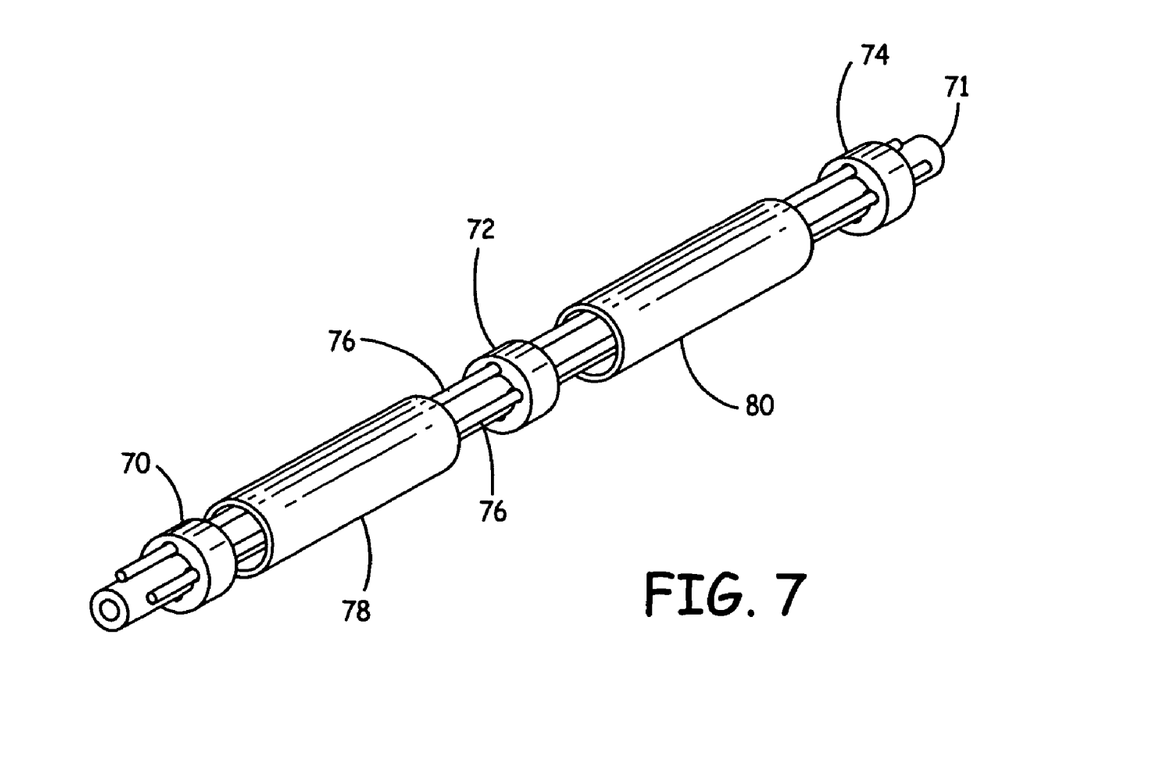
FIG. 7 illustrates an exemplary embodiment of the method adapted for imparting a different pitch or direction of wind to adjacent wire segments.

As illustrated in FIG. 6, grooves, openings or holes 58 may be provided in the twist rings 52 and 54 (also twist rings 70, 72 and 74 discussed with respect to FIG. 7). At least one groove, opening or hole 58 is provided along the inner surface of the twist rings for receiving and holding the conductor 50 (or 76). The first portion of the elongate conductor may be placed (e.g., threaded) in the groove 58 of the first twist ring 52 (or 70); the second portion of the elongate conductor may be placed (e.g., threaded) in the groove of the second twist ring 54 (or 72); and, in the case of the multi-pitch embodiment illustrated in FIG. 7, the third portion of the elongate conductor may be placed (e.g., threaded) in the groove of the third twist ring 74.

In at least one exemplary preferred embodiment, the inner elongate structure (e.g., strut) is formed with a lumen 59 adapted to guide a stylet in use of the implantable electrical lead 41. The stylet guiding lumen constitutes one exemplary embodiment of a means for guiding a stylet.

In certain exemplary embodiments, an arrangement of twist rings (e.g., twist rings 70, 72 and 74 in FIG. 7) may be employed to provide separate segments of the conductors 76 with different pitches or direction of wind from one another. In this case, the first and second twist rings 70 and 72 may define a first segment of conductor(s) 76 between the first and second twist rings, with the first segment being coiled with a first pitch and a first direction of wind following the rotation of one of the first and second twist rings 70 and 72 relative to the longitudinal axis of the inner elongate structure. The third twist ring 74, which holds a third portion of the elongate conductor, is spaced from the first and second twist rings along the length of the elongate conductor to define a second segment of the elongate conductor between the third twist ring and the whichever of the first and second twist rings is closer to the third twist ring (the second twist ring 72 in FIG. 7). The third twist ring may be rotated relative to the longitudinal axis of the inner elongate structure to coil the second segment of the elongate conductor at a second pitch or second direction of wind different than the first pitch or first direction of wind. The first and third twist rings 70 may be fixed (e.g., bonded, glued, mechanically fastened, etc.) to the elongate structure 71 subsequent to rotating the respective twist rings relative to the longitudinal axis of the inner elongate structure into their desired rotational positions.

Figure 9:
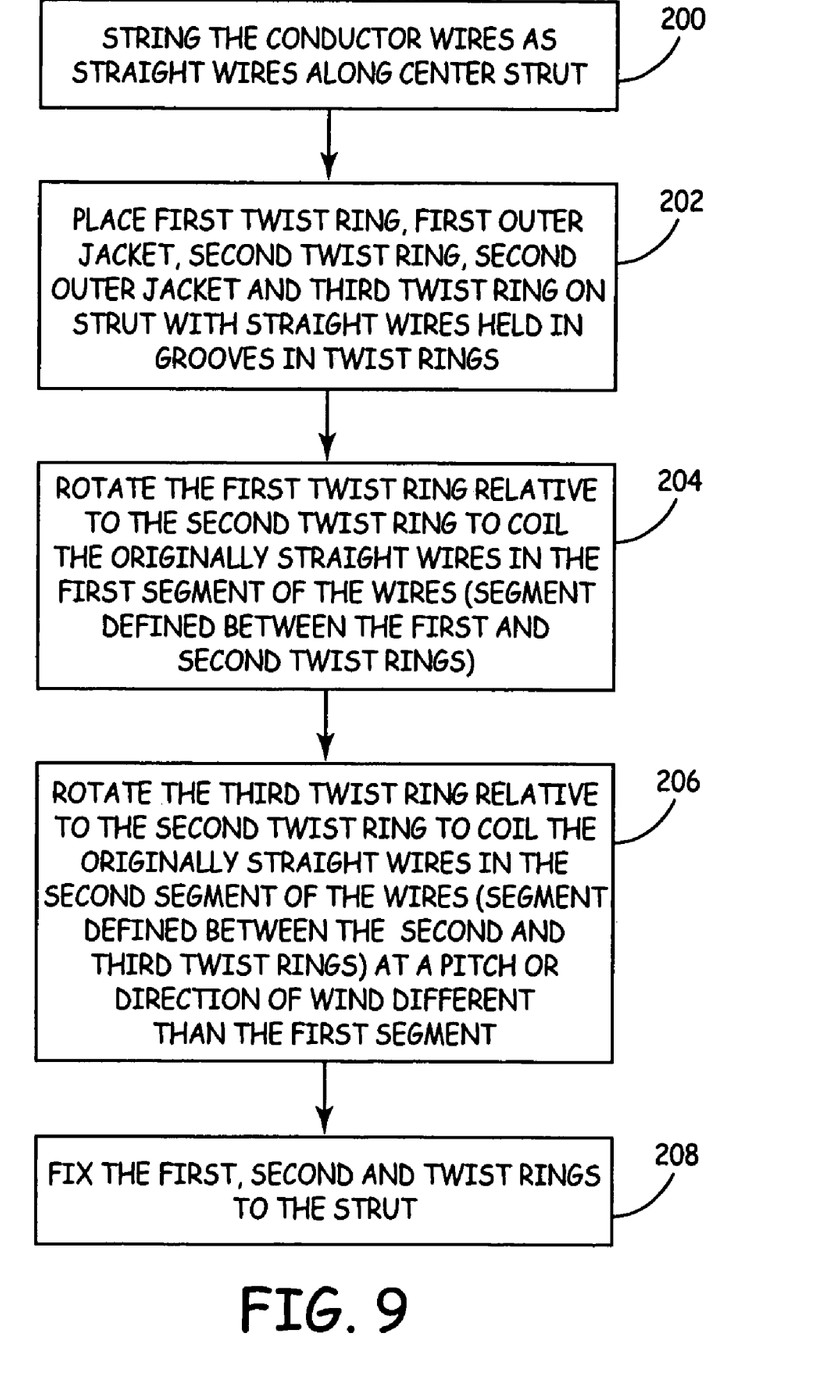

A preferred exemplary method for manufacturing a lead body having more than one pitch of conductor wire(s) 76 is illustrated in FIG. 9. This exemplary method involves (a) stringing the conductor wires 76 (FIG. 7) as straight wires along center strut 71 in step 200; (b) placing the first twist ring 70, first outer jacket 78, second twist ring 72, second outer jacket 80 and third twist ring 74 on strut 71 with straight wires held in grooves in the twist rings 70, 72 and 74 in step 202; (c) rotating the first twist ring 70 relative to the second twist ring 72 to coil the originally straight wires in the first segment of the wires (segment defined between the first and second twist rings) at step 204; (d) rotating the third twist ring 74 relative to the second twist ring 72 at step 206 to coil the originally straight wires in the second segment of the wires (segment defined between the second and third twist rings) at a pitch or direction of wind different than the first segment; and (e) fixing the first, second and third twist rings 70, 72 and 74 to the strut at step 208. Of course the order of the steps may be varied or may overlap. For example, one of the first, second and third twist rings 70, 72 and 74 may preferably be fixed to the strut 71 before the rotating steps 204 and 206.

A first outer jacket 78 may be assembled around the first segment of the conductor 76 and the inner elongate structure 71, preferably, as the twist rings 70 and 72 are placed on the strut 71; and a second outer jacket 80 may be assembled around the second segment of the conductor 76 and the inner elongate structure 71, preferably, as the twist rings 72 and 74 are placed on the strut 71. Preferably, the first, second and third twist rings 70, 72 and 74 and the first and second outer jackets 78 and 80 may have a substantially similar outer diameter such that the assembly of the outer jacket and twist rings has a substantially uniform outer diameter.

The first and third twist rings 70 may be fixed (e.g., bonded, glued, mechanically fastened, etc.) to the elongate structure 71 subsequent to rotating the respective twist rings relative to the longitudinal axis of the inner elongate structure into their desired rotational positions.

Of course, additional twist rings and coiled segments may be employed beyond that shown in FIGS. 4, 5 and 7, and the pitch or direction of wind could be varied to obtain various properties along the lead body, such as stress relief, allowance for stretch of the lead body, varying stiffness or durometer, sections adapted for engagement with an anchor, sections in which the conductors are left in a straight configuration combined with sections in which the coil is right handed, etc.

In one exemplary preferred embodiment, the conductors include (a) segments in the distal end portion 41 that are either uncoiled (straight) or nearly so (helping to keep resistance low in the segments of the conductors located in the distal end portion 41); (b) segments in a central section of the lead body 43 with a moderate pitch to fill the space between the outer jacket 60, 78 or 80 to provide strain relief to compensate for bending of the lead, reduction of stylet pinch (in embodiments in which a stylet guiding lumen is provided in the center strut), and resistance to collapse to facilitate anchoring the central section; and (c) segments in the proximal end portion 45 that may have a pitch ranging from uncoiled to tightly coiled depending upon specific application.

Preferred embodiments allow traditional lead body anchors to be used.

Exemplary embodiments may be used for any implantable tissue stimulation, such as spinal cord stimulation, brain stimulation, sacral nerve stimulation, vagal nerve stimulation, peripheral nerve stimulation, cardiac stimulation, etc.

Thus, embodiments of the implantable medical lead and method of manufacture are disclosed. One skilled in the art will appreciate that the present invention can be practiced with embodiments other than those disclosed. The disclosed embodiments are presented for purposes of illustration and not limitation.

What is claimed is:

1. A method of manufacturing an implantable electrical lead body, the method comprising:

assembling, along an outer surface of inner elongate structure defining an longitudinal axis, at least one elongate conductor and at least one twist ring holding a first portion of the elongate conductor;

fixing a second portion of the elongate conductor to the outer surface of the inner elongate structure, the second portion of the elongate conductor being spaced along the length of the elongate conductor; and rotating the twist ring relative to the longitudinal axis of the inner elongate structure to coil the at least one elongate conductor.

2. The method of claim 1 wherein the step of assembling, along an outer surface of inner elongate structure defining an longitudinal axis, at least one elongate conductor and at least one twist ring holding a first portion of the elongate conductor is performed before the step of fixing a second portion of the elongate conductor to the outer surface of the inner elongate structure, the second portion of the elongate conductor being spaced along the length of the elongate conductor.

3. The method of claim 1 wherein the step of assembling, along an outer surface of inner elongate structure defining an longitudinal axis, at least one elongate conductor and at least one twist ring holding a first portion of the elongate conductor is performed after the step of fixing a second portion of the elongate conductor to the outer surface of the inner elongate structure, the second portion of the elongate conductor being spaced along the length of the elongate conductor.

4. The method of claim 1 wherein the twist ring constitutes a first twist ring, the step of fixing a second portion of the elongate conductor to the outer surface of the inner elongate structure, the second portion of the elongate conductor being spaced along the length of the elongate conductor including:

assembling, along the outer surface of inner elongate structure, a second twist ring holding the second portion of the elongate conductor.

5. The method of claim 4 wherein the twist ring constitutes a first twist ring, the step of fixing a second portion of the elongate conductor to the outer surface of the inner elongate structure, the second portion of the elongate conductor being spaced along the length of the elongate conductor further including:

fixing the second twist ring against rotation relative to the longitudinal axis of the inner elongate structure.

6. The method of claim 5 wherein the step of fixing the second twist ring against rotation relative to the longitudinal axis of the inner elongate structure includes bonding the second twist ring to the inner elongate structure.

7. The method of claim 6 wherein the first and second twist rings define a first segment of the elongate conductor between the first and second twist rings, the first segment having a first pitch and a first direction of wind following the step of rotating the twist ring relative to the longitudinal axis of the inner elongate structure to coil the at least one elongate conductor; the method further comprising the steps of:

assembling, along the outer surface of inner elongate structure, a third twist ring holding a third portion of the elongate conductor, the third twist ring being spaced from the first and second twist rings along the length of the elongate conductor to define a second segment of the elongate conductor between the third twist ring and the whichever of the first and second twist rings is closer to the third twist ring; and rotating the third twist ring relative to the longitudinal axis of the inner elongate structure to coil the second segment of the elongate conductor at a second pitch or second direction of wind different than the first pitch or first direction of wind.

8. The method of claim 7 further comprising:

assembling a first outer jacket around the first segment of the conductor and the inner elongate structure; and assembling a second outer jacket around the second segment of the conductor and the inner elongate structure; and wherein the first, second and third twist rings have an outer diameter; and the first and second outer jackets have an outer diameter substantially similar to the outer diameter of the first, second and third twist rings such that the assembly of the outer jacket and twist ring has a substantially uniform outer diameter.

9. The method of claim 8 further comprising:

fixing the first twist ring to the elongate structure subsequent to the step of rotating the twist ring relative to the longitudinal axis of the inner elongate structure to coil the at least one elongate conductor; and fixing the third twist ring to the elongate structure subsequent to the step of rotating the third twist ring relative to the longitudinal axis of the inner elongate structure to coil the second segment of the elongate conductor at a second pitch or second direction of wind different than the first pitch or first direction of wind.

10. The method of claim 9 wherein the steps of fixing the first and second twist rings to the elongate structure include bonding the first and second twist rings to the elongate structure.

11. The method of claim 5 wherein the first and second twist rings define a segment of the elongate conductor between the first and second twist rings, the method further comprising:

assembling a first outer jacket around the first segment of the conductor and the inner elongate structure; and wherein the first and second twist rings have an outer diameter; and the first and second outer jackets have an outer diameter substantially similar to the outer diameter of the first and second twist rings such that the assembly of the outer jacket and twist ring has a substantially uniform outer diameter.

12. The method of claim 4 wherein the first and second twist rings define a segment of the elongate conductor between the first and second twist rings, the method further comprising:

assembling a first outer jacket around the first segment of the conductor and the inner elongate structure; and wherein the first and second twist rings have an outer diameter; and the first and second outer jackets have an outer diameter substantially similar to the outer diameter of the first and second twist rings such that the assembly of the outer jacket and twist ring has a substantially uniform outer diameter.

13. The method of claim 10 wherein:

the first and second twist rings have an inner surface defining at least one groove for receiving and holding the conductor;

the step of assembling, along an outer surface of inner elongate structure defining an longitudinal axis, at least one elongate conductor and at least one twist ring holding a first portion of the elongate conductor includes placing the first portion of the elongate conductor in the groove of the first twist ring; and the step of assembling, along the outer surface of inner elongate structure, a second twist ring holding the second portion of the elongate conductor includes placing the second portion of the elongate conductor in the groove of the second twist ring.

14. The method of claim 6 wherein:

the first and second twist rings have an inner surface defining at least one groove for receiving and holding the conductor;

the step of assembling, along an outer surface of inner elongate structure defining an longitudinal axis, at least one elongate conductor and at least one twist ring holding a first portion of the elongate conductor includes placing the first portion of the elongate conductor in the groove of the first twist ring; and the step of assembling, along the outer surface of inner elongate structure, a second twist ring holding the second portion of the elongate conductor includes placing the second portion of the elongate conductor in the groove of the second twist ring.

15. The method of claim 4 wherein:
the first and second twist rings have an inner surface defining at least one groove for receiving and holding the conductor;
the step of assembling, along an outer surface of inner elongate structure defining an longitudinal axis, at least one elongate conductor and at least one twist ring holding a first portion of the elongate conductor includes placing the first portion of the elongate conductor in the groove of the first twist ring; and
the step of assembling, along the outer surface of inner elongate structure, a second twist ring holding the second portion of the elongate conductor includes placing the second portion of the elongate conductor in the groove of the second twist ring.

16. The method of claim 5 further comprising fixing the first twist ring against rotation relative to the longitudinal axis of the inner elongate structure subsequent to the step of rotating the twist ring relative to the longitudinal axis of the inner elongate structure to coil the at least one elongate conductor.

17. The method of claim 16 wherein the steps of fixing the first and second twist rings against rotation relative to the longitudinal axis of the inner elongate structure include bonding the first and second twist rings to the elongate structure.

18. The method of claim 1 further comprising fixing the first twist ring to the elongate structure subsequent to the step of rotating the twist ring relative to the longitudinal axis of the inner elongate structure to coil the at least one elongate conductor.

19. The method of claim 18 wherein the steps of fixing the first twist ring to the elongate structure include bonding the first twist ring to the elongate structure.

20. The method of claim 1 wherein the at least one conductor comprises a plurality of conductors.

21. The method of claim 1 wherein the at least one conductor comprises braided stranded wire.

22. The method of claim 1 further comprising forming the inner elongate structure with a lumen adapted to guide a stylet when the lead body is used in an implantable electrical lead.

23. An implantable electrical lead comprising:
proximal and distal end portions, and a lead body extending between the proximal and distal end portions;
at least one electrical contact in the proximal end portion adapted to make electrical contact with a connector of a lead extension or pulse generator;
at least one electrode in the distal end portion adapted to interact with tissue;
at least one elongate conductor through the lead body between the proximal and distal portions in electrical communication with the contact and electrode, the conductor including along its length at least a first portion, a second portion spaced along the length of conductor from the first portion, and a first segment defined between the first and second portions;
wherein the lead body includes:
an inner elongate structure defining an longitudinal axis;
first and second twist rings mounted on the inner elongate structure, the first and second twist rings holding the first and second portions, respectively, of the elongate conductor, one of the first and second twist rings having been rotated about the inner elongate structure relative to the other of the first and second twist rings to coil the first segment of the elongate conductor, both twist rings having been bonded to the inner elongate structure; and
an outer jacket covering the inner elongate structure and first segment of the elongate conductor between the first and second twist rings.

24. The implantable electrical lead of claim 23 wherein the at least one elongate conductor comprises a plurality of elongate conductors, each having a first coiled segment between the first and second twist rings.

25. The implantable electrical lead of claim 24 wherein:
the first coiled segments of the elongate conductors have a first pitch and direction of wind;
the lead body further includes a third twist ring mounted on the inner elongate structure and holding a third portion of each of the elongate conductors, the third twist ring being spaced from the first and second twist rings to define a second segment of each of the elongate conductors; and
the third twist ring having been rotated about the inner elongate structure to coil the second segment of each of the elongate conductor at a different pitch or direction of wind than the first coiled segments, the third twist ring then having been bonded to the inner elongate structure.

26. The implantable electrical lead of claim 25 wherein the inner elongate structure comprises a tubular structure having a lumen for guiding a stylet.

27. The implantable electrical lead of claim 26 wherein the tubular structure comprises:
a first tubular section having a first stiffness and opposite ends; and
a second tubular section having a second stiffness different than the first stiffness, the second tubular section having opposite ends, one of which is bonded to one of the ends of the first tubular section.

28. The implantable electrical lead of claim 27 wherein the first tubular section has a different durometer than the second tubular section.

29. The implantable electrical lead of claim 23 wherein the inner elongate structure comprises:
a first elongate section having a first stiffness and opposite ends; and
a second elongate section having a second stiffness different than the first stiffness, the second elongate section having opposite ends, one of which is bonded to one of the ends of the first elongate section.

30. The implantable electrical lead of claim 29 wherein the first elongate section has a different durometer than the second elongate section.

31. The implantable electrical lead of claim 23 wherein:
the first segment of the elongate conductor has a first pitch and direction of wind;
the lead body further includes a third twist ring mounted on the inner elongate structure and holding a third portion of the elongate conductor, the third twist ring being spaced from the first and second twist rings to define a second segment of the elongate conductor; and
the third twist ring having been rotated about the inner elongate structure to coil the second segment of the elongate conductor at a different pitch or direction of wind than the first segment, the third twist ring then having been bonded to the inner elongate structure.

32. An implantable electrical lead comprising:
proximal and distal end portions, and a lead body extending between the proximal and distal end portions;
electrical contact means in the proximal end portion for making electrical contact with a connector of a lead extension or pulse generator;

electrode means in the distal end portion for interacting with tissue;

wire conductor means, through the lead body between the proximal and distal portions, for establishing electrical communication between the electrical contact means and the electrode means, the wire conductor means including a plurality of wire conductors each having a length with a first portion, a second portion spaced along the length of wire conductor from the first portion, and a first segment defined between the first and second portions;

wherein the lead body includes:

an inner elongate structure defining an longitudinal axis;

first and second twist rings mounted on the inner elongate structure, the first and second twist rings holding the first and second portions, respectively, of the elongate conductors, one of the first and second twist rings having been rotated about the inner elongate structure relative to the other of the first and second twist rings to coil the first segments of the elongate conductors, both twist rings being fixed to the inner elongate structure before use of the lead; and an outer jacket covering the inner elongate structure and first segments of the elongate conductors between the first and second twist rings.

33. The implantable electrical lead of claim 32 wherein:

the first segments of the elongate conductors have a first pitch and direction of wind;

the lead body further includes a third twist ring mounted on the inner elongate structure and holding a third portion of each of the elongate conductors, the third twist ring being spaced from the first and second twist rings to define a second segment of each of the elongate conductors; and the third twist ring having been rotated about the inner elongate structure to coil the second segment of each of the elongate conductor at a different pitch or direction of wind than the first coiled segments, the third twist ring then having been bonded to the inner elongate structure.

34. The implantable electrical lead of claim 32 wherein the inner elongate structure includes means for guiding a stylet.

35. The implantable electrical lead of claim 32 wherein the inner tubular structure comprises:

a first tubular section having a first stiffness and opposite ends; and a second tubular section having a second stiffness different than the first stiffness, the second tubular section having opposite ends, one of which is bonded to one of the ends of the first tubular section.

36. The implantable electrical lead of claim 35 wherein the first tubular section has a different durometer than the second tubular section.

37. A method of manufacturing an implantable electrical lead body, the method comprising:

(a) providing an elongate strut, first and second twist rings, and at least one conductor, the first and second twist rings having at least one opening or groove for receiving and holding at least one conductor;

(b) fixing the first twist ring to the strut;

(c) threading the at least one conductor wire through the opening or groove in the first twist ring;

(d) placing a second twist ring on the strut wherein upon conclusion of steps (b) and (d) the first and second twist rings are spaced apart along the strut;

(e) threading the at least one conductor through the opening or groove in the second twist ring, wherein steps (b) through (e) may be performed in any order and upon conclusion of steps (b) through (e) a segment of the at least one conductor is defined between the first and second twist rings;

(f) rotating the second twist ring relative to the longitudinal axis of the strut to coil the segment of at least one elongate conductor between the first and second twist rings; and (g) fixing the second twist ring to the strut.

38. The method of claim 37 further comprising placing an outer jacket over the strut before only one of steps (b) of fixing the first twist ring to the strut, and (d) of placing the second twist ring to the strut.

39. The method of claim 38 wherein the step of placing the outer jacket over the strut is performed after step (b) of fixing the first twist ring to the strut and before step (d) of placing the second twist ring to the strut.

40. The method of claim 39 wherein the step of placing the outer jacket over the strut is performed after step (c) of threading the at least one conductor wire through the opening or groove in the first twist ring.

41. The method of claim 39 wherein the step of placing the outer jacket over the strut is performed before step (c) of threading the at least one conductor wire through the opening or groove in the first twist ring.

42. The method of claim 37 wherein the steps (b) of fixing the first twist ring to the strut, and (g) of fixing the second twist ring to the strut include bonding the twist ring to the strut.

43. The method of claim 37 wherein the segment of the at least one conductor between the first and second twist rings constitutes a first segment having a first pitch and first direction of wind, the method further comprising:

(h) placing a third twist ring on the strut wherein upon conclusion of steps (b), (c) and (h) the first, second and third twist rings are spaced apart along the strut, the third twist ring having an opening or groove;

(i) threading the at least one conductor through the opening or groove in the third twist ring, wherein steps (b) through (e) and (h) through (i) may be performed in any order and upon conclusion thereof a second segment of the at least one conductor is defined between the third twist ring and one of the first and second twist rings;

(j) rotating the third twist ring relative to the longitudinal axis of the strut to coil the second segment of the at least one elongate conductor at a second pitch or second direction of wind different than the first pitch or first direction of wind; and (g) fixing the third twist ring to the strut.

44. The method of claim 43 further comprising:

before only one of steps (b) of fixing the first twist ring to the strut, and (d) of placing the second twist ring to the strut, placing a first outer jacket portion over the strut such that upon conclusion of steps (b) and (d) the first outer jacket portion is arranged between the first and second twist rings; and before the step (h) of placing the third twist ring, placing a second outer jacket portion over the strut such that upon conclusion of steps (b), (d) and (h) the second outer jacket portion is arranged between the third twist ring and one of the first and second twist rings.

* * * * *